US00PP23500P2

(12) United States Plant Patent
Kawashima et al.

(10) Patent No.: US PP23,500 P2
(45) Date of Patent: Mar. 26, 2013

(54) **NEW GUINEA *IMPATIENS* PLANT NAMED 'SAKIMP022'**

(50) Latin Name: *Impatiens×hybrida (I. hawkeri)*
Varietal Denomination: SAKIMP022

(75) Inventors: Moriya Kawashima, Amstelveen (NL); Michiyoshi Fuyama, Shizuoka (JP)

(73) Assignee: Sakata Seed Corporation, Yokohama (JP)

( * ) Notice: Subject to any disclaimer, the term of this patent is extended or adjusted under 35 U.S.C. 154(b) by 0 days.

(21) Appl. No.: 13/373,455

(22) Filed: Nov. 15, 2011

(51) Int. Cl.
*A01H 5/00* (2006.01)

(52) U.S. Cl. ..... Plt./318.7

(58) Field of Classification Search ..... Plt./318.7
See application file for complete search history.

*Primary Examiner* — Annette Para
(74) *Attorney, Agent, or Firm* — Jondle & Associates, P.C.

(57) ABSTRACT

A new New Guinea *Impatiens* plant named 'SAKIMP022' particularly distinguished by cherry red flower color, strong root system and a spreading plant growth habit is described.

1 Drawing Sheet

Genus and species: *Impatiens×hybrida* (*I. hawkeri*).
Variety denomination: 'SAKIMP022'.

BACKGROUND OF THE NEW PLANT

The present invention comprises of a new and distinct cultivar of New Guinea *Impatiens*, botanically known as *Impatiens×hybrida* (*I. hawkeri*), and referred to by the variety name 'SAKIMP022'. 'SAKIMP022' originated from a controlled hybridization conducted in June 2004 between New Guinea *Impatiens* 'NC-35②', an unpatented proprietary breeding line with an orange flower color and New Guinea *Impatiens* 'NC-229A', an unpatented proprietary breeding line with a lilac flower color.

The $F_1$ plants were evaluated in Misato, Japan in an open field trial. The criteria for plant selection included a beautiful cherry red flower color, strong root system and a spreading plant growth habit. At the completion of the trial, one single-plant selection was made based on the above criteria and vegetatively propagated. From May to August 2006, the selection was evaluated in an open field in Misato, Japan. The selection subsequently was named 'SAKIMP022' and found to have its unique characteristics reproduce true to type in successive generations of asexual propagation.

Plant Breeder's Rights for this variety have not been applied for and 'SAKIMP022' has not been made publicly available more than one year prior to filing of this application.

SUMMARY OF THE INVENTION

The following are the most outstanding and distinguishing characteristics of this new variety when grown under normal horticultural practices in a greenhouse in Salinas, Calif.

1. Cherry red flower color;
2. Strong root system; and
3. Spreading plant growth habit.

DESCRIPTION OF PHOTOGRAPHS

This New Guinea *Impatiens* plant is illustrated by the accompanying photographs which show overall plant habit including blooms, buds, and foliage of the plant. The colors shown are as true as can be reasonably obtained by conventional photographic procedures. The photographs are of a plant about five months old, grown in a greenhouse in Salinas, Calif.

Figure 1:
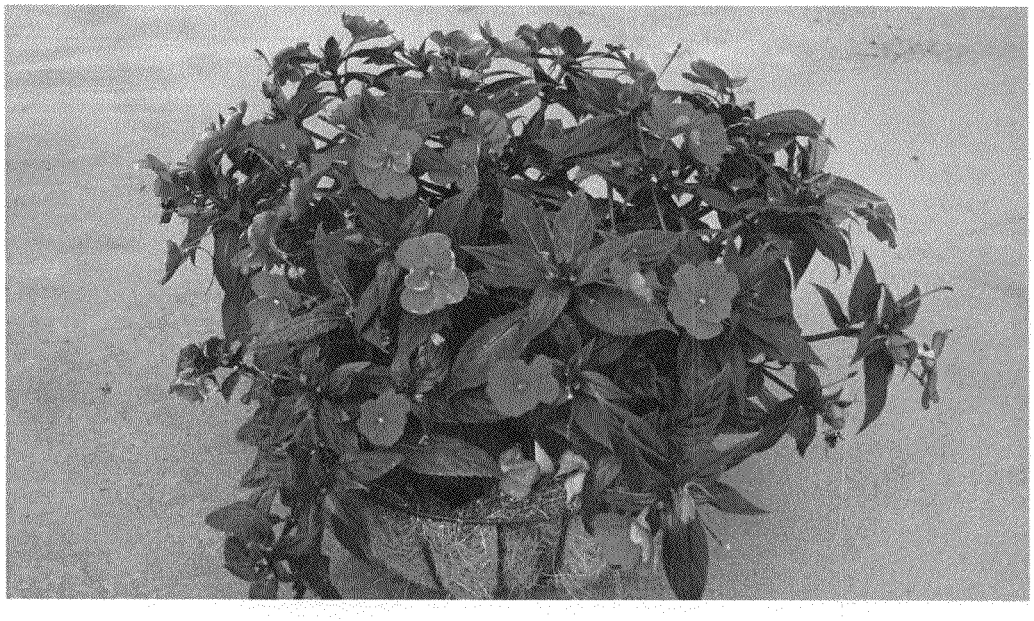
Figure 2:
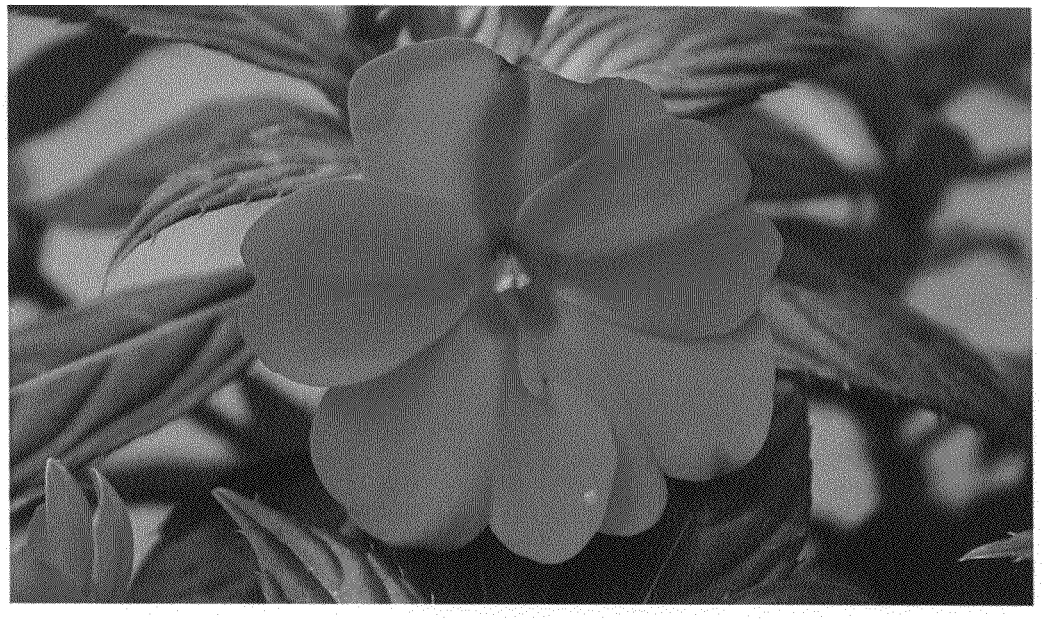

FIG. 1 shows the overall plant habit.
FIG. 2 shows the mature inflorescence.

DESCRIPTION OF THE NEW VARIETY

The following traits and characteristics that describe the new variety were obtained from plants grown about five months from propagation by terminal cutting in Salinas, Calif., under greenhouse conditions. Color references are to The Royal Horticultural Society Colour Chart, 4th edition (2001). Anatomic labels are from *The Cambridge Illustrated Glossary of Botanical Terms*, by M. Hickey and C. King, Cambridge University Press.

DETAILED BOTANICAL DESCRIPTION OF THE NEW PLANT

Classification:
- *Family.*—Balsaminaceae.
- *Botanical.*—*Impatiens×hybrida* (*I. hawkeri*).
- *Common name.*—New Guinea *Impatiens.*

Parentage:
- *Female parent.*—Proprietary New Guinea *Impatiens* plant line 'NC-35②'.
- *Male parent.*—Proprietary New Guinea *Impatiens* plant line 'NC-229A'.

Growth:
- *Growth and branching habit.*—Spreading.
- *Height.*—25.0 cm to 26.0 cm from soil line to top of foliage.
- *Width.*—44.0 cm to 45.0 cm.
- *Propagation.*—Vegetative cuttings.
- *Time to produce a finished flowering plant.*—6 to 8 weeks.
- *Time to initiate and develop roots.*—Approximately 4 weeks.
- *Environmental conditions for plant growth.*—The terminal 1.0 to 1.5 inches of an actively growing stem was excised. The vegetative cuttings were propagated in five to six weeks. The base of the cuttings were dipped for 1 to 2 seconds in a 1:9 solution of Dip 'N Grow (1 solution: 9 water) root inducing solution immediately prior to sticking into the cell trays. Cuttings were stuck into plastic cell trays having 98 cells, and containing a moistened peat moss-based growing medium. The cuttings were misted with water from overhead for 10 seconds every 30 minutes until sufficient roots were formed. Rooted cuttings were transplanted and grown in 6-inch plastic pots in a glass greenhouse located in Salinas, Calif. Pots contained a peat moss-based growing medium. Soluble fertilizer containing 20% nitrogen, 10% phosphorus and 20% potassium was applied once a day or every other day by overhead irrigation. Plants were fertilized every 2-3 days, 2 times in consecutive applications and then given one clear water application. Pots were top-dressed with a dry, slow release fertilizer containing 14% nitrogen, 14% phosphorus and 14% potassium. The typical average air temperature was 24° C.

*Temperature tolerances*.—Plants observed to continue flowering in a temperature range of 5° C. to 36° C. Plants can withstand high heat and humidity.

Branches:

*Average number*.—3 main branches, 11 total.

*Length of branches*.—Approximately 2.0 cm from soil line to first node, approximately 20.0 cm total.

*Diameter of branches*.—Main branch is 8.0 mm.

*Stem color*.—RHS 187A (Greyed-purple).

Stems:

*Color*.—RHS 187B (Greyed-purple).

*Anthocyanin color*.—RHS 187B (Greyed-purple).

*Pubescence*.—Absent.

*Description*.—Strong; circular cross-section, smooth and shiny.

*Size*.—Length: 12.0 cm to 13.0 cm. Diameter: 6.0 mm.

*Internode length*.—4.0 cm.

Leaves:

*Arrangement*.—Whorled with up to 5 leaves per node, opposite if only two leaves at one node.

*Size*.—*Length:* 9.5 cm. Width: 2.8 cm.

*Shape*.—Lanceolate, curled.

*Apex*.—Acuminate.

*Base*.—Attenuate.

*Margin*.—Ciliate.

*Color*.—Upper surface: Darker than RHS 147A (Yellow-green). Lower surface: RHS 147B (Yellow-green).

*Leaf variegation*.—Absent.

*Leaf fragrance*.—Absent.

*Texture* (*both surfaces*).—Dull, waxy.

*Surface pubescence*.—Glabrous.

*Venation*.—Pinnate.

*Venation color*.—Upper surface: RHS 147D (Yellow-green). Lower surface: RHS 187C (Greyed-purple).

*Petioles*.—Length: 1.0 cm. Diameter: 0.4 cm. Color: RHS 187C (Greyed-purple). Texture: Smooth, glabrous.

Flower buds:

*Shape*.—Deltoid, longitudinal cross-section.

*Surface*.—Glabrous.

*Size*.—Length: 1.6 cm. Diameter: 1.2 cm.

*Color*.—RHS 59A (Red-purple).

Inflorescence:

*Inflorescence type*.—Single flower with spur.

*Number of flowers per node*.—1 to 3 in bloom, about 4 to 6 flower buds per node.

*Number of flowers per plant*.—Approximately 20 in bloom.

*Flowering season*.—Will flower so long as temperature is above 5° C.

*Lastingness of individual blooms on the plant*.—14 days.

*Fragrance*.—Absent.

*Peduncle*.—Color: RHS 187C (Greyed-purple). Size: Length: 4.0 cm. Diameter: 2.0 mm. Texture: Smooth, glabrous.

Corolla:

*Shape*.—Roughly circular with 5 radial petals.

*Size*.—Diameter: Approximately 6.0 cm. Depth: 1.0 cm.

*Petals*.—Shape: Obcordate. Apex: Emarginate (cleaved). Base: Attenuate. Margin: Entire. Pubescence: Glabrous. Size: Length: 3.5 cm. Width: 2.0 cm. Color: Upper surface: Closest to but darker than RHS N57A (Red-purple). Lower surface: Closest to RHS 58B (Red-purple). Eye zone: Closest to RHS 60A (Red-purple). Texture (both surfaces): Soft, smooth.

*Calyx* (*sepals*).—Shape: Lanceolate. Number: 2. Color: RHS 187D (Greyed-purple). Length: 1.0 cm. Diameter: 0.5 cm. Base: Subcordate. Apex: Caudate. Margin: Entire. Texture: Glabrous.

Spur:

*Shape*.—Tubular; curved downward.

*Color*.—Closest to RHS 58C (Red-purple).

*Size*.—Length: 4.5 cm. Diameter: 2.0 mm.

Reproductive organs:

*Stamens*.—Form: Fused; split into 4 lobes. Number: Many. Filament color: RHS 58A (Red-purple). Filament length: 5.0 mm. Pollen number: Abundant. Pollen color: RHS 155D (White). Pollen description: Powdery. Anther length: 4.0 mm. Anther color: RHS 155A (White).

*Pistils*.—Number: 5. Stigma color: RHS 143A (Green). Style color: RHS 143A (Green). Style length: 5.0 mm. Ovary arrangement: Parietal. Ovary color: RHS 143A (Green).

Fruit and seed set: No seed set observed.

Disease and insect resistance: No particular resistance or susceptibility has been observed.

COMPARISON WITH PARENTAL AND COMMERCIAL VARIETIES

'SAKIMP022' differs from female parent 'NC-35②' by having red colored flowers, while 'NC-35②' has orange colored flowers.

'SAKIMP022' differs from male parent 'NC-229A' by having red colored flowers, while 'NC-229A' has lilac colored flowers.

'SAKIMP022' is most similar to the commercial *Impatiens* 'SunPatiens® Vigorous Red' (varietal denomination 'Misato FG1') (U.S. Plant Pat. No. 17,708); however, there are differences as listed in the table below:

TABLE 1

| Comparison with Similar Variety | | |
|---|---|---|
| Characteristic | 'SAKIMP022' | 'Misato FG1' |
| Petal color, upper surface | Closest to, but darker than RHS N57A (Red-Purple) | Closest to RHS 46C (Red) |
| Petal color, lower surface | Closest to RHS 58B (Red-Purple) | RHS 58C (Red-Purple) |
| Petal color, eye zone | Closest to RHS 60A (Red-Purple) | RHS 60D (Red-Purple) |
| Plant growth habit | Spreading | Vigorous |

We claim:

1. A new and distinct variety of New Guinea *Impatiens* plant named 'SAKIMP022' as shown and described herein.

* * * * *